US 11,734,750 B2

(12) United States Patent
Pekarek-Kostka et al.

(10) Patent No.: US 11,734,750 B2
(45) Date of Patent: Aug. 22, 2023

(54) SYSTEMS, MEDIA, AND METHODS FOR STAGGERED MEDICAL TRANSACTIONS

(71) Applicant: MicroPharmacy Corporation, Wethersfield, CT (US)

(72) Inventors: Peter Pekarek-Kostka, Middletown, CT (US); John E. Kulesza, Wethersfield, CT (US)

(73) Assignee: Micropharmacy Corporation, Wethersfield, CT (US)

( * ) Notice: Subject to any disclaimer, the term of this patent is extended or adjusted under 35 U.S.C. 154(b) by 204 days.

(21) Appl. No.: 16/877,691

(22) Filed: May 19, 2020

(65) Prior Publication Data

US 2021/0366030 A1 Nov. 25, 2021

(51) Int. Cl.
*G06Q 30/00* (2023.01)
*G06Q 30/0601* (2023.01)
(Continued)

(52) U.S. Cl.
CPC ..... *G06Q 30/0643* (2013.01); *G06F 16/9554* (2019.01); *G06Q 20/3276* (2013.01); *G16H 20/10* (2018.01)

(58) Field of Classification Search
CPC ........... G06Q 30/0643; G06Q 20/3276; G16H 20/10; G06F 16/9554
(Continued)

(56) References Cited

U.S. PATENT DOCUMENTS 7,127,432 B2 * 10/2006 Rubin .................. G06Q 20/383
705/74
8,190,481 B2 * 5/2012 Green .................... G06Q 10/10
705/21

(Continued)

FOREIGN PATENT DOCUMENTS

| CN | 107194782 A | 9/2017 |
|----|-------------|--------|
| CN | 109949892 A | 6/2019 |
| CN | 110706404 A | 1/2020 |

OTHER PUBLICATIONS

U. B. Ceipidor, C. M. Medaglia, A. Marino, S. Sposato and A. Moroni, KerNeeS: A protocol for mutual authentication between NFC phones and POS terminals for secure payment transactions, 2012, 2012 9th International ISC Conference on Information Security and Cryptology, pp. 115-120. (Year: 2012).*

U.B. Ceipider, C. M. Medaglia, A. Marino, S. Sposato and A. Moroni, KerNeeS: A protocol for mutual authentication between NFC phones and POS terminals for secure payment transactions, 2012, 2012 91h international ISC Conference on information Security and Cryptology, pp. 118-120. (Year: 2012).*

*Primary Examiner* — Jeffrey A. Smith
*Assistant Examiner* — Brittany E Bargeon
(74) *Attorney, Agent, or Firm* — Dinsmore & Shohl LLP; Weston R. Gould (57) ABSTRACT

Systems, media and methods for staggered medical transactions are provided. A method includes displaying a plurality of products on a display client. The method may further include receiving, at the display client, input from a user selecting a product. The method may also further include prompting the user via the display client to continue on another device. The method may additionally include outputting, via the display client, an identifier associated (Continued)

with the product and the user. The method may also additionally include receiving the identifier at a user device after the user has been authenticated at the user device. The method may still further include receiving confirmation input at the user device from the user confirming selection of the product. The method may also still further include outputting, from the user device, the confirmation data based upon the confirmation input.

17 Claims, 5 Drawing Sheets

(51) Int. Cl.
*G06F 16/955* (2019.01)
*G16H 20/10* (2018.01)
*G06Q 20/32* (2012.01)

(58) Field of Classification Search
USPC .................................................. 705/27.2
See application file for complete search history.

(56) References Cited

U.S. PATENT DOCUMENTS

| | | | | |
|---|---|---|---|---|
| 8,898,751 | B2* | 11/2014 | Yin | G06F 21/42 726/5 |
| 9,646,295 | B1* | 5/2017 | Kanuganti | G06Q 20/325 |
| 10,770,173 | B2* | 9/2020 | Mathew | G06Q 20/3223 |
| 2015/0074008 | A1* | 3/2015 | Guillama | G06Q 50/265 705/325 |
| 2015/0186892 | A1* | 7/2015 | Zhang | G06Q 20/40145 705/44 |
| 2016/0044385 | A1* | 2/2016 | Kareeson | G06Q 20/3224 725/27 |
| 2017/0161728 | A1* | 6/2017 | Satyanarayan | G06Q 20/363 |
| 2017/0201524 | A1* | 7/2017 | Dureau | H04N 21/25841 |
| 2017/0220761 | A1* | 8/2017 | Toupin | G16H 20/10 |
| 2017/0323299 | A1* | 11/2017 | Davis | G06Q 20/204 |
| 2017/0330188 | A1* | 11/2017 | Canh | H04L 63/0838 |
| 2018/0130548 | A1* | 5/2018 | Fisher | G06Q 20/3227 |
| 2018/0137480 | A1* | 5/2018 | Houghton, IV | G06F 1/1694 |
| 2018/0285880 | A1* | 10/2018 | Jerstroem | G06Q 20/327 |

* cited by examiner

SYSTEMS, MEDIA, AND METHODS FOR STAGGERED MEDICAL TRANSACTIONS

BACKGROUND

Patients sometimes purchase items while at their doctor's office. As doctor's offices become more modern, many now utilize large interactive screens to add to patient convenience for a variety of purposes, such as providing information (medical information, office hours, etc.), allowing patients to check in/out, and the like. However, within the confines of a waiting room, fulfilling patient purchases of medical products on a waiting room screen can trigger privacy and regulatory implications.

Accordingly, a need exists for systems that provide patients with purchasing convenience and privacy, along with media and methods of use of such systems.

SUMMARY

In one embodiment, a system may include a display client comprising memory and a processor coupled to the memory, with the processor being configured to display a plurality of products. The processor may also be configured to receive input selecting a product from a user positioned in front of the display client. The processor may additionally be configured to prompt the user to continue on another device. The processor may be further configured to output an identifier associated with the product and the user. The system may also include a user device configured to receive the identifier after the user has been authenticated at the user device. The user device may be further configured to receive confirmation input from the user confirming selection of the product. The user device may also be configured to output the confirmation data based upon the confirmation input.

In another embodiment, a method may comprise displaying a plurality of products on a display client. The method may also include receiving, at the display client, input from a user selecting a product. The method may further include prompting the user via the display client to continue on another device. The method may still further include outputting, via the display client, an identifier associated with the product and the user. The method may additionally include receiving the identifier at a user device after the user has been authenticated at the user device. The method may additionally also include receiving confirmation input at the user device from the user confirming selection of the product. The method may still additionally include outputting, from the user device, the confirmation data based upon the confirmation input.

In yet another embodiment, a non-transitory computer readable medium embodies computer-executable instructions, that when executed by a processor, cause the processor to display a plurality of products on a display client. The processor may also receive, at the display client, input from a user selecting a product. The processor may further prompt the user via the display client to continue on another device. The processor may additionally output, via the display client, an identifier associated with the product and the user. The processor may additionally receive the identifier at a user device after the user has been authenticated at the user device. The processor may further still receive confirmation input at the user device from the user confirming selection of the product. The processor may still additionally output, from the user device, the confirmation data based upon the confirmation input.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Embodiments of the present disclosure are directed to methods, systems, and media for staggered medical product transactions. For example, a patient in the waiting room of a doctor's office may want to purchase a product shown on a display client. The display client may be available for the patient to learn more about the product, and if desired, to purchase the product. However, having a patient purchase certain products around others may implicate privacy, regulatory, and/or data security concerns. To address these concerns, the display client may offer the patient the ability to continue their transaction elsewhere. For example, the user may provide their contact information (email, phone number, etc.) and/or obtain an identifier (number, bar code, QR code, etc.) to continue the purchase on their user device (smartphone, tablet, laptop, etc.). In this way, patients can enjoy the convenience of using the display client to initiate a purchase in a way that addresses privacy, regulatory, and/or data security concerns.

Figure 1:
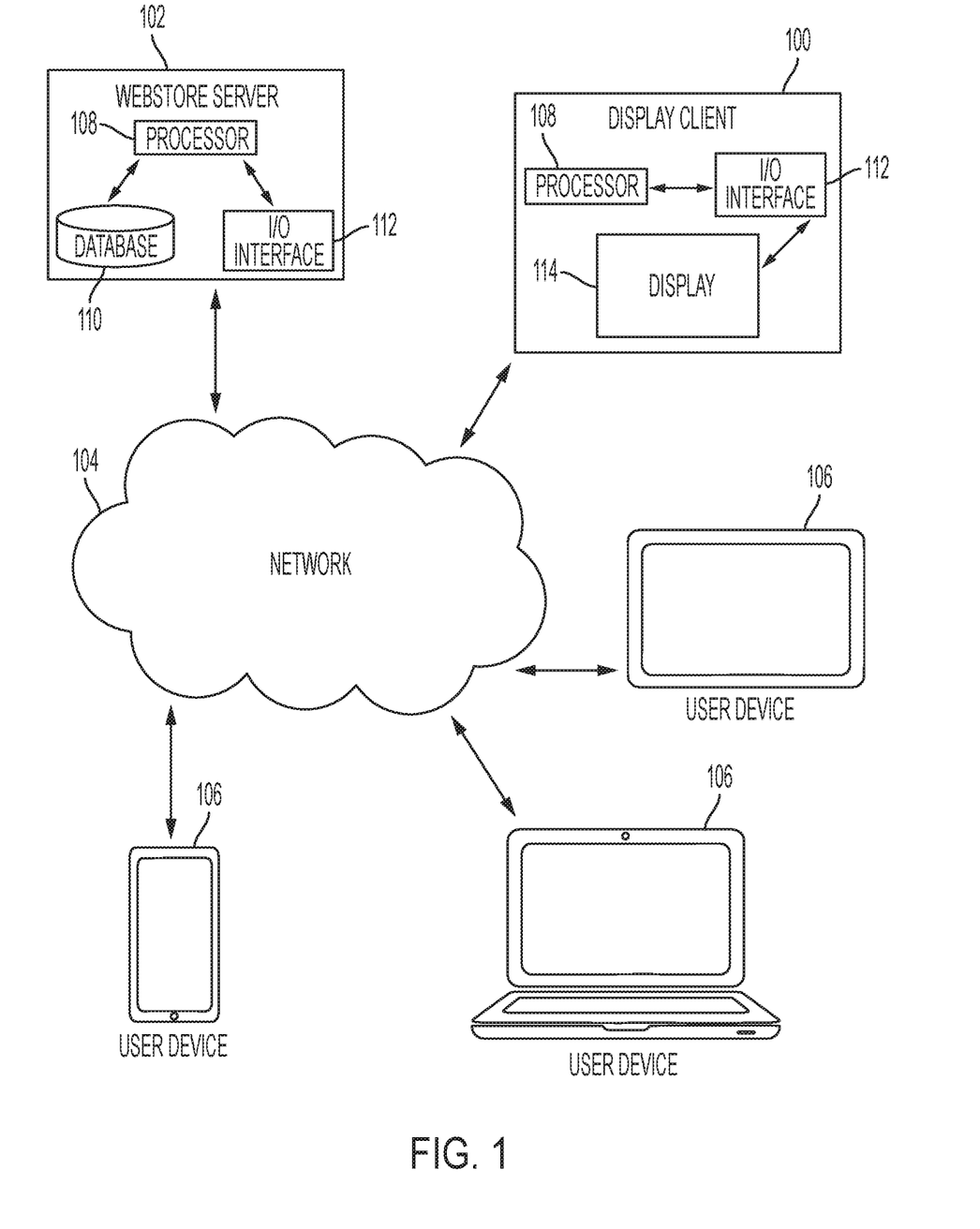
FIG. 1 schematically illustrates an exemplary operating environment featuring a display client, user devices, and a remote server, according to one or more embodiments shown and described herein.

Referring now to FIG. 1, an exemplary operating environment featuring a display client, user devices, and a remote server is shown according to various embodiments. A display client 100 is depicted as being in communication over a network 104 with a server 102 and user devices 106. The display client 100 may include a processor 108 in communication with an input/output (I/O) interface 112. The I/O interface 112 may be in communication with a display 114. Any suitable type of processor 108, I/O interface 112, and/or display 114 may be used in any suitable configuration and quantities within the display client 100. For example, one or more processors 108 may be in direct or indirect communication with any component of the display client 100. In one embodiment, the display 114 may be a touch screen. In another embodiment, the I/O interface may utilize cameras in the display client for gaze tracking and/or gesture/movement tracking of a user interacting with the display client 100.

The display client 100 may be connected to one or more networks 104, which may include, by way of non-limiting example, LTE, WiMAX, UMTS, CDMA, and GSM. The display client 100 may communicate through the network 104 with the server 102. In this embodiment, the server 102 is a webstore server that includes a processor 108 in communication with a database 110 and an I/O interface 112 to manage transactions. The server 102 may utilize the database 110 (i.e., back-end) to manage transactions received from the display client 100 and/or user devices 106. The I/O interface 112 may provide any suitable type of interface (i.e., front-end), such as a webpage/website, which may provide output to and receive input from the display client 100 and/or user devices 106. In this embodiment, any quantity/type of server or other computer device(s) may be utilized in any suitable remotely-accessible configuration (cloud, server cluster, stand-alone server, etc.).

The display client 100 and/or server 102 may be in communication via the network 104 with one or more user devices 106. In some embodiments, a user device 106 may communicate directly with a display client 100 without a network 104, such as via Bluetooth, near field communication (NFC), and the like. A user device 106 may include any suitable type of computing device, such as by way of non-limiting examples, smartphones, tablets, laptops, desktops, or any other type of computing device.

Figure 2A:
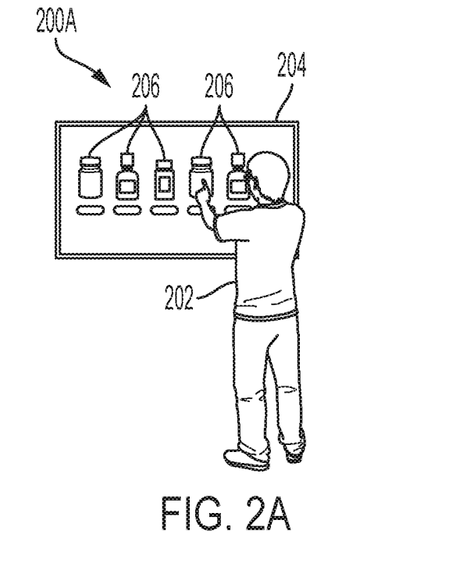
FIG. 2A schematically illustrates an exemplary operating environment featuring a user browsing products on a display client, according to one or more embodiments shown and described herein.

Referring now to FIG. 2A, an exemplary operating environment 200A featuring a user browsing products on a display client is shown according to various embodiments. In this embodiment, a user 202 utilizes a touch-screen display client 204 to browse available products. In other embodiments, the display client 204 may receive input from a user 202 via a mouse and/or keyboard, via gaze tracking of the eyes of the user 202, and/or gesture tracking of the user 202 (e.g., the user points at a product to select it and waves their hand/arm to scroll through the products). Any suitable type and/or size of display client 204 may be utilized. The products 206 in this embodiment are products for sale in the offices/waiting rooms of medical, chiropractic, dental, vision, and other healthcare providers (creams, ointments, nutritional supplements, equipment, wearable items, or any other items that may be available for sale at a practitioner's office). Any type of product 206 can be provided in other embodiments. In this embodiment, the display client 204 is publicly available within the office/waiting room, such that it does not authenticate the user 202. A display client 204 may be utilized by any number of users 202 throughout the day. In some embodiments, the display client 204 may have a privacy screen such that only a user 202 standing directly in front of the display client 204 can see what is displayed on the display client 204.

Figure 2B:
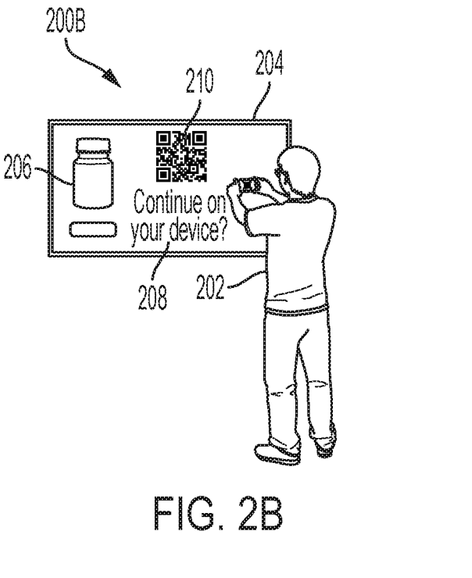
FIG. 2B schematically illustrates the exemplary operating environment of FIG. 2A wherein the user obtains an identifier from the display client, according to one or more embodiments shown and described herein.

Referring now to FIG. 2B, the exemplary operating environment 200B of FIG. 2A wherein the user obtains an identifier from the display client is shown according to various embodiments. A user 202 has selected a particular product 206 they are interested in purchasing (e.g., placing it in their virtual shopping cart). In this embodiment, a prompt 208 is provided to the user 202 to continue/finalize the transaction elsewhere. To facilitate this, an identifier associated with the user 202 and the product 206 is provided to the user 202. In this embodiment, the identifier is provided with a QR code that can be scanned by the user's device. In other embodiments, other identifiers such as barcodes or alphanumeric identifiers may be provided. In still other embodiments, the prompt 208 may request information from the user 202 such as an email address, phone number, social media contact information, or any other information by which the user 202 can receive details to continue the transaction. For example, the display client 204 and/or a server may send a link via the user's email, phone number, or social media account to go to a website to complete the transaction. In still other embodiments, the user 202 may be a repeat customer/patient such that they can authenticate at the display client 204 via a password, biometrics, gesture verification, direct proximity-limited communication of the user device with the display client 204, and the like.

Figure 2C:
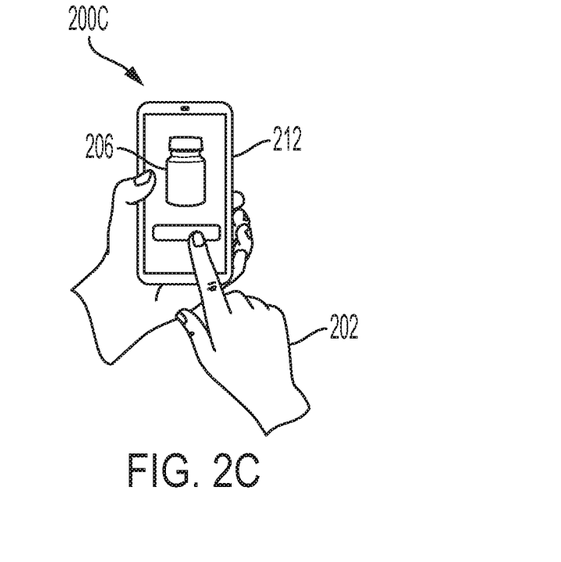
FIG. 2C schematically illustrates the exemplary operating environment of FIG. 2B wherein the user continues the transaction on their user device, according to one or more embodiments shown and described herein.

Referring now to FIG. 2C, the exemplary operating environment 200C of FIG. 2B wherein the user continues the transaction on their user device is shown according to various embodiments. Although a smartphone 212 is depicted, as stated herein, any suitable type of device may be utilized by the user 202 to complete their transaction. In various embodiments, the transaction may be completed in the office/waiting room or elsewhere by the user 202. The user 202 may authenticate on their user smartphone 212 utilizing any suitable mechanisms such as passwords/passcodes, 2-factor authentication, biometric verification, gesture verification, and the like. The user 202 may have continued the transaction by accessing a link on their smartphone (via email, text/SMS, social media app, etc.), by scanning an identifier presented on the display client 204 (such as a QR code 210), and the like. The user 202 may then complete their purchase of the product 206 on their smartphone 212, for example.

Figure 3:
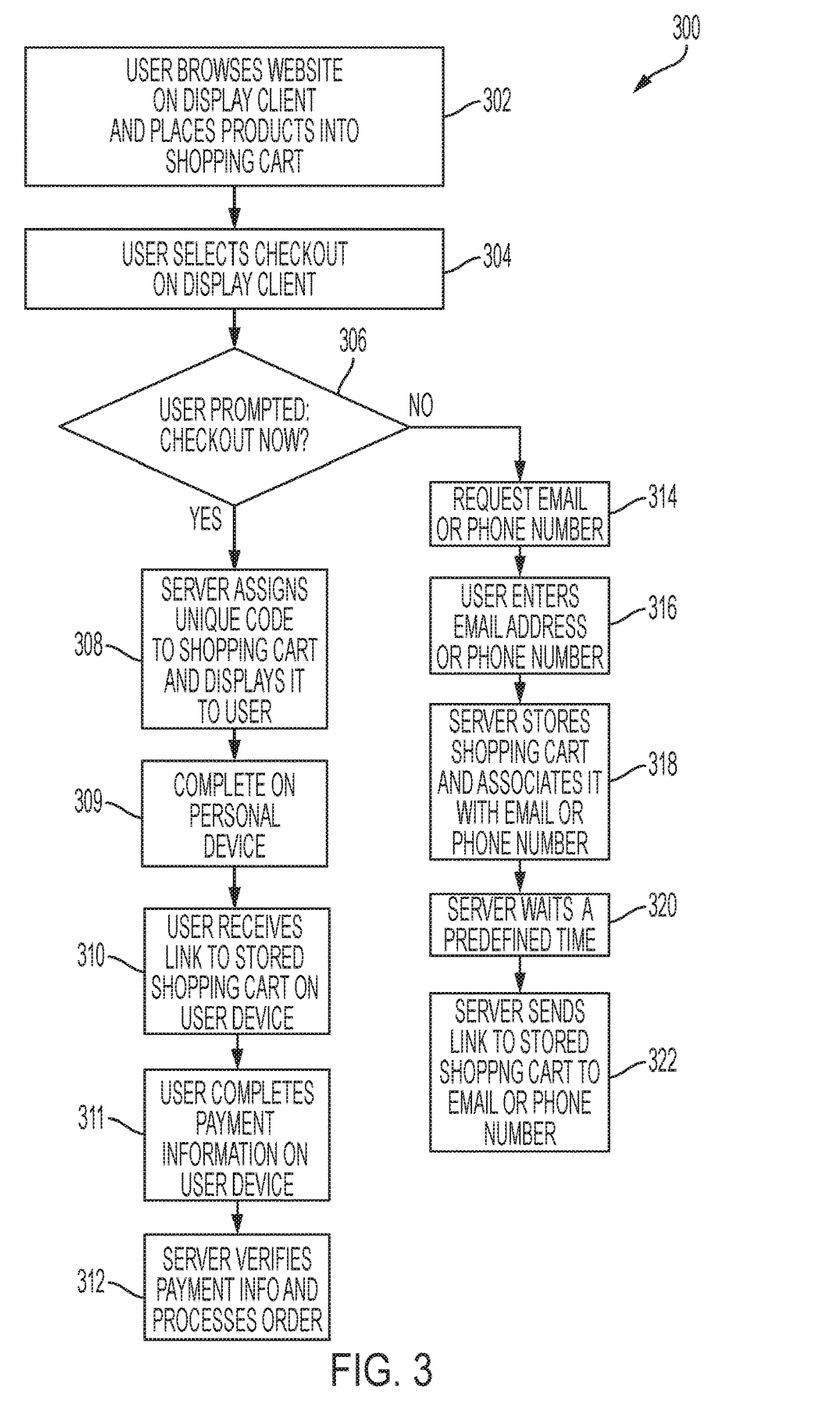
FIG. 3 is a flow diagram depicting exemplary interaction of a user utilizing a display client and their user device to purchase a product, according to one or more embodiments shown and described herein.

Referring now to FIG. 3, a flow diagram 300 of exemplary interaction of a user utilizing a display client and their user device to purchase a product is shown according to various embodiments. At block 302, a user may browse a website (or other interface) on a display client and place products into their shopping cart. At block 304, the user may select an option to checkout on the display client to bring up a checkout interface. At block 306, a determination is made to confirm whether the user is ready to checkout. If the user indicates that they are ready to checkout, then at block 308, the server may assign a unique code to the shopping cart and display it to the user. At block 309, the transaction may be transferred for completion on the user's personal device. At block 310, the user may receive a link on their device (sent by the display client or server) to the stored shopping cart. At block 311, the user may complete payment information on their device. At block 312, the server may verify the payment information and process the order.

Returning to block 306, if a determination is made at the display client that the user is not ready to check out, then at block 314, the user's email and/or phone number may be requested. In some embodiments, other contact information such as social media profile information may be utilized. At block 316, the user may enter their email address and/or phone number. At block 318, the server may store the shopping cart and associate it with the user's email and/or phone number. At block 320, the server may wait a predefined period of time. In other embodiments, there may be no server waiting period. At block 322, the server may send a link to the stored shopping cart to the email and/or phone number for later completion. In some embodiments, the link and/or shopping cart may have an expiration date/time.

Figure 4:
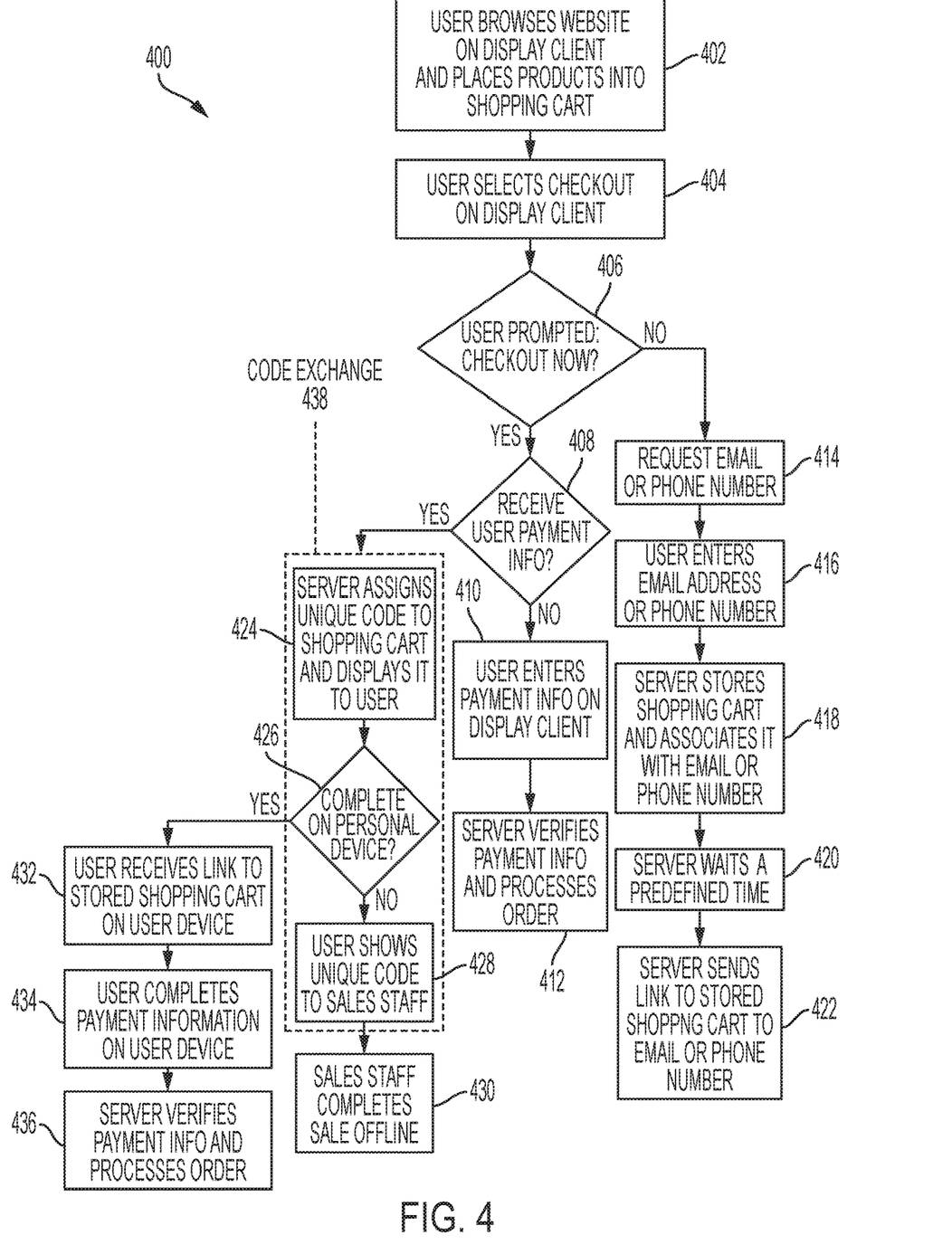
FIG. 4 is a flow diagram depicting exemplary interaction of a user purchasing a product utilizing a variety of options, according to one or more embodiments shown and described herein.

Referring now to FIG. 4, a flow diagram 400 of exemplary interaction of a user purchasing a product utilizing a variety of options is shown according to various embodiments. At block 402, a user may browse a website on a display client and place products into their shopping cart. At block 404, the user may select an option to checkout on the display client in order to bring up a checkout interface. At block 406, a determination is made to confirm whether the user is ready to checkout. If a determination is made at the display client that the user is not ready to check out, then at block 314, the user's email and/or phone number may be requested. At block 316, the user may enter their email address and/or phone number. At block 318, the server may store the shopping cart and associates it with the email and/or phone number. At block 320, the server may wait a predefined period of time. At block 322, the server may send a link to the stored shopping cart to the email and/or phone number.

Returning to block 406, if a determination is made that the user is ready to checkout, then at block 408 a determination is made as to whether user payment information has been received at the display client. If so, then at block 410 the user may enter their payment information on the display client. At block 412 the server may verify payment information and process the order.

Returning to block 408, if a determination is made that the user payment information is not received, then at block 424 the server may assign a unique code to the shopping cart and display it to the user. As discussed herein, this may take the form of an alphanumeric code, a QR code, a barcode, and the like, depending upon how the code is to be used (i.e., used on the user device, shown to sales staff, etc.). At block 426 a determination is made as to whether the transaction will be completed on the user's personal device. If not, then at block 428 the user may show the unique code to sales staff. A code exchange 438 occurs between blocks 424 and 428, wherein the unique transaction code is provided by the display client to the user and sales staff. At block 430 the sales staff may complete the sale offline using the code.

Returning to block 426, if a determination is made that the transaction will be completed on the user's personal device, then at 432 the user may receive a link on their device directed to the stored shopping cart. At block 434, the user may complete payment information on their device. At block 436, the server may verify the payment information and process the order. In some embodiments, the server may receive the identifier output by the display client, output the identifier to the user device, and receive the confirmation input from the user device.

Figure 5:
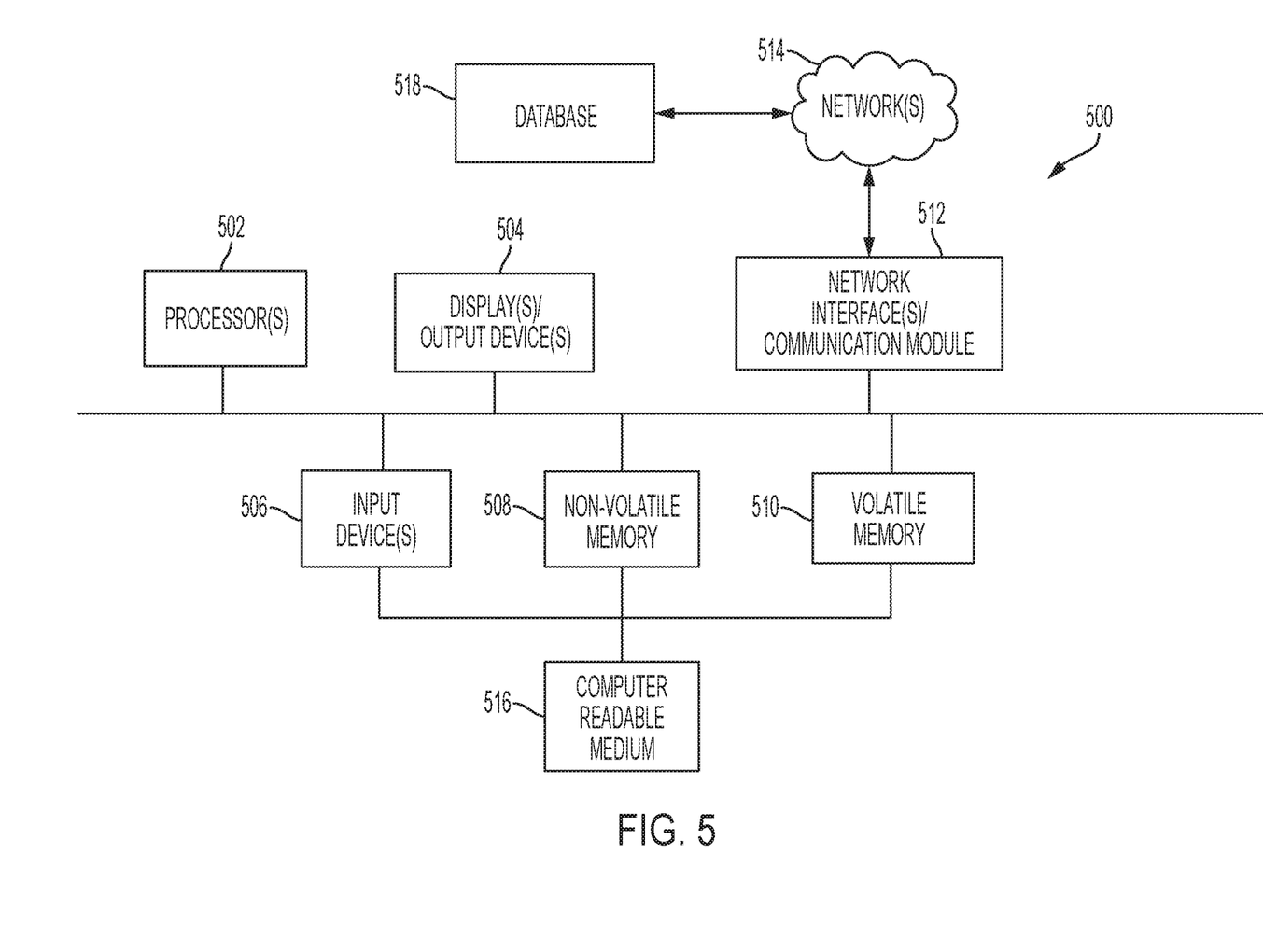
FIG. 5 is a block diagram illustrating computing hardware utilized in one or more display clients, user devices, and servers, according one or more embodiments shown and described herein.

Turning now to FIG. 5, a block diagram illustrates an exemplary computing device 500, through which embodiments of the disclosure can be implemented. The computing device 500 described herein is but one example of a suitable computing device and does not suggest any limitation on the scope of any embodiments presented. The computing device 500 in some embodiments may also be utilized to implement a display client 100, a server 102, a user device 106 and/or any combination thereof. Nothing illustrated or described with respect to the computing device 500 should be interpreted as being required or as creating any type of dependency with respect to any element or plurality of elements. In various embodiments, a computing device 500 may include, but need not be limited to, a desktop, laptop, server, client, tablet, smartphone, or any other type of device that can utilize data. In an embodiment, the computing device 500 includes at least one processor 502 and memory (non-volatile memory 508 and/or volatile memory 510). The computing device 500 can include one or more displays and/or output devices 504 such as monitors, speakers, headphones, projectors, wearable-displays, holographic displays, and/or printers, for example. Output devices 504 may further include, for example, a display 114 and/or speakers of the display client 100, a display and/or speakers of a server 102, a display and/or speakers of a user device 106, devices that emit energy (radio, microwave, infrared, visible light, ultraviolet, x-ray and gamma ray), electronic output devices (Wi-Fi, radar, laser, etc.), audio (of any frequency), etc.

The computing device 500 may further include one or more input devices 506 which can include, by way of example, any type of mouse, keyboard, disk/media drive, memory stick/thumb-drive, memory card, pen, touch-input device, biometric scanner, voice/auditory input device, motion-detector, camera, scale, and the like. Input devices 506 may further include sensors, cameras, sensing components of a display client 100, server 102, and/or user device 106 (touch screen, buttons, accelerometer, light sensor, etc.), and any device capable of measuring data such as motion data (accelerometer, GPS, magnetometer, gyroscope, etc.), biometric (blood pressure, pulse, heart rate, perspiration, temperature, voice, facial-recognition, motion/gesture tracking, gaze tracking, iris or other types of eye recognition, hand geometry, fingerprint, DNA, dental records, weight, or any other suitable type of biometric data, etc.), video/still images, and audio (including human-audible and human-inaudible ultrasonic sound waves). Input devices 506 may include cameras (with or without audio recording), such as digital and/or analog cameras, still cameras, video cameras, thermal imaging cameras, infrared cameras, cameras with a charge-couple display, night-vision cameras, three-dimensional cameras, webcams, audio recorders, and the like.

The computing device 500 typically includes non-volatile memory 508 (ROM, flash memory, etc.), volatile memory 510 (RAM, etc.), or a combination thereof. A network interface 512 can facilitate communications over a network 514 via wires, via a wide area network, via a local area network, via a personal area network, via a cellular network, via a satellite network, etc. Suitable local area networks may include wired Ethernet and/or wireless technologies such as, for example, wireless fidelity (Wi-Fi). Suitable personal area networks may include wireless technologies such as, for example, IrDA, Bluetooth, Wireless USB, Z-Wave, ZigBee, and/or other near field communication protocols. Suitable personal area networks may similarly include wired computer buses such as, for example, USB and FireWire. Suitable cellular networks include, but are not limited to, technologies such as LTE, WiMAX, UMTS, CDMA, and GSM. Network interface 512 can be communicatively coupled to any device capable of transmitting and/or receiving data via one or more network(s) 514, such as network 104. Accordingly, the network interface hardware 512 can include a communication transceiver for sending and/or receiving any wired or wireless communication. For example, the network interface hardware 512 may include an antenna, a modem, LAN port, Wi-Fi card, WiMax card, mobile communications hardware, near-field communication hardware, satellite communication hardware and/or any wired or wireless hardware for communicating with other networks and/or devices. The database 110 is depicted as being within the server 102 but in other embodiments one or more databases 110 may be external to the server 102 and accessed via the network(s) 104 to remotely access data and store data.

A computer-readable medium 516 may comprise a plurality of computer readable mediums, each of which may be either a computer readable storage medium or a computer readable signal medium. A computer readable storage medium may reside, for example, within an input device 506, non-volatile memory 508, volatile memory 510, or any combination thereof. A computer readable storage medium can include tangible media that is able to store instructions associated with, or used by, a device or system. A computer readable storage medium includes, by way of example: RAM, ROM, cache, fiber optics, EPROM/Flash memory, CD/DVD/BD-ROM, hard disk drives, solid-state storage, optical or magnetic storage devices, diskettes, electrical connections having a wire, or any combination thereof. A computer readable storage medium may also include, for example, a system or device that is of a magnetic, optical, semiconductor, or electronic type. Computer readable storage media and computer readable signal media are mutually exclusive.

A computer readable signal medium can include any type of computer readable medium that is not a computer readable storage medium and may include, for example, propagated signals taking any number of forms such as optical, electromagnetic, or a combination thereof. A computer readable signal medium may include propagated data signals containing computer readable code, for example, within a carrier wave. Computer readable storage media and computer readable signal media are mutually exclusive.

The computing device 500 may include one or more network interfaces 512 to facilitate communication with one or more remote devices, which may include, for example, client and/or server devices. This is depicted, for example, as the network 104 in FIG. 1, although any suitable network configuration may be utilized. A network interface 512 may also be described as a communications module, as these terms may be used interchangeably.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

The order of execution or performance of the operations in examples of the disclosure illustrated and described herein is not essential, unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

It is noted that the terms "substantially" and "about" and "approximately" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A system comprising:
a display client comprising memory and a processor coupled to the memory, the display client configured to be housed in a healthcare provider site and provide public access to a plurality of unauthenticated users, the processor configured to:
  display a plurality of products to an unauthenticated user;
  receive input selecting a product from a user positioned in front of the display client;
  prompt the user to continue on a private user device; and
  output an identifier associated with the product and the user to the user device;
the user device configured to:
  receive the identifier after the user has been authenticated at the user device;
  receive confirmation input from the user confirming selection of the product; and
  output confirmation data to a remote server based upon the confirmation input, the remote server at a location different than a location of the display client and the private user device, the remote server in network communication with the display client and the private user device; said system configured to provide secure sale of said product.

2. The system of claim 1, wherein the display client is further configured to receive input via at least one of a touchscreen, gesture tracking, and gaze tracking.

3. The system of claim 1, wherein the prompt comprises an identifier configured to be scanned by the user device.

4. The system of claim 3, wherein the identifier is a QR code.

5. The system of claim 1, further comprising a remote device configured to:
receive the identifier output by the display client;
output the identifier to the user device; and
receive the confirmation input from the user device.

6. The system of claim 1, wherein:
prompting the user to continue on another device further comprises the display client being configured to receive user contact information comprising an email address or phone number; and
the display client being further configured to send the identifier to the user device via the contact information.

7. A method comprising:
displaying a plurality of products on a public display client housed in a healthcare provider site and configured to provide access to unauthenticated users;
receiving, at the display client, input from an unauthenticated user selecting a product;
prompting the user via the display client to continue on a private user device;
outputting, via the display client, an identifier associated with the product and the user;
receiving the identifier at the private user device after the user has been authenticated at the private user device;

receiving confirmation input at the user device from the user confirming selection of the product;

outputting to a remote server, from the user device, confirmation data based upon the confirmation input, the remote server at a location different than a location of the display client and the private user device, the remote server in network communication with the display client and the private user device.

8. The method of claim 7 further comprising receiving input via the display client, wherein the display client is configured to receive input via at least two of a touchscreen, gesture tracking, and gaze tracking.

9. The method of claim 7, wherein the prompt comprises an identifier and the method further comprises scanning, via the user device, the identifier displayed on the display client.

10. The method of claim 9, wherein the identifier is a QR code.

11. The method of claim 7 further comprising:
receiving, at a remote device, the identifier output by the display client;
outputting, at the remote device, the identifier to the user device; and
receiving the confirmation input from the user device.

12. The method of claim 7 further comprising:
prompting the user to continue on another device by receiving, at the display client, user contact information comprising an email address or phone number; and
sending the identifier from the display client to the user device via the contact information.

13. A non-transitory computer readable medium embodying computer-executable instructions, that when executed by a processor, cause the processor to execute operations comprising:
displaying a plurality of products on a display client housed in a healthcare provider site and providing public access to a plurality of unauthenticated users;
receiving, at the display client, input from an unauthenticated user selecting one or more of the products;
prompting the user via the display client to continue on a private user device;
outputting, via the display client, an identifier associated with the product and the user;
receiving the identifier at the private user device after the user has been authenticated at the private user device;
receiving confirmation input at the private user device from the user confirming selection of the product;
outputting to a remote server, from the private user device, confirmation data based upon the confirmation input, the remote server at a location different than a location of the display client and the private user device, the remote server in network communication with the display client and the private user device.

14. The non-transitory computer readable medium of claim 13 embodying further computer-executable instructions that comprise receiving input via the display client, wherein the display client is configured to receive input via at least two of a touchscreen, gesture tracking, and gaze tracking.

15. The non-transitory computer readable medium of claim 13, wherein the prompt comprises an identifier and the method further comprises scanning, via the user device, the identifier displayed on the display client.

16. The non-transitory computer readable medium of claim 13 embodying further computer-executable instructions that comprise:
receiving, at a remote device, the identifier output by the display client;
outputting, at the remote device, the identifier to the user device; and
receiving the confirmation input from the user device.

17. The non-transitory computer readable medium of claim 13 embodying further computer-executable instructions that comprise:
prompting the user to continue on another device by receiving, at the display client, user contact information comprising an email address or phone number; and
sending the identifier from the display client to the user device via the contact information.

* * * * *